United States Patent [19]

Shields

[11] Patent Number: 4,617,148

[45] Date of Patent: Oct. 14, 1986

[54] OPAQUE LIQUID HAND SOAP

[75] Inventor: Susan J. Shields, New Castle County, Del.

[73] Assignee: Hercules Incorporated, Wilmington, Del.

[21] Appl. No.: 617,784

[22] Filed: Jun. 6, 1984

Related U.S. Application Data

[63] Continuation-in-part of Ser. No. 509,748, Jun. 30, 1983, abandoned.

[51] Int. Cl.$^4$ .......................... C11D 1/12; C11D 3/37; C11D 17/08
[52] U.S. Cl. .................................. 252/547; 252/117; 252/173; 252/174.17; 252/174.23; 252/546; 252/550; 252/552; 252/555; 252/557; 252/558; 252/DIG. 2; 252/DIG. 5; 252/DIG. 13; 252/DIG. 14; 252/DIG. 15
[58] Field of Search ...................... 252/174.17, 174.18, 252/174.23, DIG. 2, DIG. 5, DIG. 13, DIG. 14, DIG. 15, 173, 96

[56] References Cited

U.S. PATENT DOCUMENTS

| | | | |
|---|---|---|---|
| 4,072,632 | 2/1978 | Reed | 252/541 |
| 4,323,467 | 4/1982 | Fu | 252/106 |
| 4,330,438 | 5/1982 | Dierassi et al. | 424/70 |
| 4,338,211 | 7/1982 | Stiros | 252/142 |
| 4,414,144 | 11/1983 | Hebowitz et al. | 252/552 |
| 4,420,410 | 12/1983 | Huttinger | 252/117 |
| 4,434,089 | 2/1984 | Billington et al. | 252/547 |
| 4,472,297 | 9/1984 | Bolich, Jr. et al. | 252/550 |
| 4,491,539 | 1/1985 | Hoskins et al. | 252/174.17 |

FOREIGN PATENT DOCUMENTS

| | | |
|---|---|---|
| 1955557 | 5/1971 | Fed. Rep. of Germany |
| 1235292 | 6/1971 | United Kingdom |

OTHER PUBLICATIONS

Natrosol (R) Hydroxyethylcellulose a Nonionic Water-Soluble Polymer, Hercules Incorporated, Rev. 10-80, Wilmington, Delaware 19899.

*Primary Examiner*—Prince E. Willis
*Assistant Examiner*—Hoa Van Le
*Attorney, Agent, or Firm*—Joanne L. Horn

[57] ABSTRACT

Disclosed is an opaque liquid composition suitable for use as a soap, primarily a liquid hand soap, which is thickened with a water-soluble polymer, such as, hydroxyethyl cellulose or hydroxypropyl guar.

14 Claims, No Drawings

OPAQUE LIQUID HAND SOAP

This invention relates to opaque liquid compositions suitable for use as hand soaps. More specifically, this invention refers to such compositions having an active ingredient concentration of less than ten percent (10%) which are thickened with a water-soluble polymer.

Liquid compositions useful as hand soaps are well-known in the cosmetic field, however, they did not gain public acceptance until the late 70's. Since then they have been making inroads into a segment of the marketplace which was previously the exclusive domain of the bar soap.

Usually, opaque liquid hand soaps contain a detergent, a primary lathering agent, and an opacifying agent (which opacifying agent can also act as a secondary thickening agent) in a water carrier as the principal ingredients.

Until the present time, opaque liquid hand soaps have generally been formulated with at least fifteen percent (15%) active ingredients, and have been thickened with sodium chloride. Unfortunately, sodium chloride tends to lessen the lathering characteristics of the liquid hand soap, to dry out the skin surfaces, and to be highly irritating to the eyes. Hence, the opaque liquid hand soaps presently available are not as versatile as their competition, the bar soap.

Thus, there is a need for an opaque liquid hand soap having improved lathering characteristics which will gently cleanse the skin without drying the skin after routine use. Soaps which do not dry out the skin surfaces, but tend to soften and soothe surface tissues are said to be emollient. Thus, the more emollient a soap the milder it is to the skin surfaces. Further, the more emollient a soap, the less likely it is to irritate the eyes.

According to this invention, there is provided an opaque liquid hand soap composition containing a water-soluble polymer thickening agent which exhibits improved lather characteristics, which imparts superior lubricity and emollience to the skin surfaces, and contains less than 10% of active ingredients. Specifically, this invention relates to an opaque liquid hand soap composition based on an anionic surfactant detergent, a primary lathering agent selected from the group consisting of anionic and amphoteric surfactants or mixtures thereof, and a water-soluble hydroxyethyl cellulose or water-soluble hydroxypropyl guar containing clearly defined amounts of the hydroxyalkyl group as the primary thickening agent, and a nonionic surfactant opacifying agent as its principal or essential components, all of which are dissolved in a water vehicle.

More specifically, the hydroxyethyl cellulose is one having a hydroxyethyl substitution from about 1.8 to about 3.6 M.S., preferably from about 2.0 to about 3.0 M.S., and a water viscosity from about 1500 centipoise (cps.) to about 5000 cps. at 25° C. at 1% concentration at 30 rpm. The molecular substitution (M.S.) for hydroxyethyl cellulose is defined as the average number of moles of hydroxyethyl substituent groups present per anhydroglucose unit.

The hydroxypropyl guar is one having a hydroxypropyl substitution from about 0.3 to about 1.2 M.S., preferably from about 0.3 to about 0.9 M.S. The molecular substitution (M.S.) for hydroxypropyl guar is defined as the average number of moles of hydroxypropyl substituent groups present per anhydrohexose unit.

In commercial practice, the concentrations of the principal ingredients can and do vary widely. In most commercial formulations, the principal ingredients, which should add up to 100%, are within the following concentration ranges:

| Principal Ingredients | Percent by weight based on the principal ingredients |
| --- | --- |
| Anionic surfactant detergent | 40–90 |
| Primary lathering agent | 20–50 |
| Primary thickener | 0.5–20 |
| Nonionic surfactant opacifying agent | 5–30 |

Water, preferably at a concentration of from about 85% to about 94% by weight of the total composition, is the vehicle for the ingredients. In commercially available liquid based soaps, water is typically present at a concentration of from about 75% to about 85%.

The hydroxyethyl cellulose which can be used as a primary thickener in the compositions of this invention is prepared by reacting ethylene oxide with cellulose and a strongly alkyline medium. Specific techniques for carrying out the etherification are well known in the art and any known procedure can be employed. See, for example, Whistler, R. L. & BeMiller, J. N., *Industrial Gums*, p. 650 (2ed. 1973). The hydroxyethyl cellulose useful in the practice of this invention is also available commercially from Hercules Incorporated.

The hydroxypropyl guar gum can be prepared by the method of U.S. Pat. No. 3,700,612.

The concentration of hydroxyethyl cellulose or the hydroxypropyl guar in the composition of this invention is from about 0.5% to about 20% by weight based on the principal ingredients. Desirably the water-soluble polymeric thickener is present at a concentration from about 10% to about 17%.

The detergent is an anionic surfactant, the key functional property of which is detergency. Suitable anionic surfactants which mainly function as detergents include (1) alkylbenzenesulfonates of the formula:

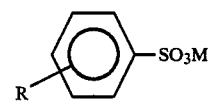

where R is dodecyl and M is sodium, calcium, triethanolammonium, and isopropylammonium; (2) alpha-olefinsulfonates of the formula:

$$R'CH=CHSO_3Na$$

where R' is 10–18 carbon atoms and mixtures thereof, preferably 10–16 carbon atoms and mixtures thereof; and (3) alkyl sulfates of the formula $R''OSO_3M'$ where R'' is lauryl and M' is sodium, potassium, ammonium, diethanolammonium, and triethanolammonium. The preferred anionic surfactant is a mixture of sodium alphaolefin sulfonates containing 10 to 14 carbon atoms.

The primary lathering agent can be an anionic or amphoteric surfactant or mixtures thereof which function chiefly as foaming or lathering agents. Such anionic surfactants include (1) dialkyl sulfosuccinates of the formula: $RO_2CCH_2CH(SO_3Na)CO_2R$, where R is a lauryl or myristyl; (2) N-acyl-sarcosinates of the formula: $R'CON(CH_3)CH_2CO_2Na$, where R'CO— is lauroyl and cocoyl; (3) sodium N-acyl-N-methyltaurates of the formula: R″CON(CH₃)CH₂CH₂SO₃Na, where R″CO is acyl, such as oleyl, cocoyl, palmitoyl and tall oil; and (4) sodium cocoylisothionate. Typical amphoteric surfactants include amidopropylbetaines of the formula: R‴CONHCH₂CH₂CH₂N⁺(CH₃)₂CH₂CO₂⁻, where R‴CO is cocoyl and lauroyl. The preferred lathering agent is sodium lauroyl sarcosinate.

Any nonionic surfactant whose key functional property is opacification can be used as the opacifying agent. Suitable opacifying surfactants include glycol esters of fatty acids, glycerol esters of fatty acids, and monoalkanolamides of fatty acids. Typical glycol esters of fatty acids include ethylene glycol monostearate, propylene glycol monostearate, and diethylene glycol monostearate. Glycerol esters of fatty acids suitable for use as opacifying agents in the liquid hand soap of this invention include glycerol monostearate and glycerol monolaurate. The ethanolamide of stearic acid and the isopropanolamide of stearic acid are typical monoalkanolamides of fatty acids. The preferred opacifying agent is ethylene glycol monostearate.

In addition to the principal ingredients mentioned above, a typical liquid hand soap will frequently contain other conventional additives, such as a secondary lathering agent, skin substantive aids, chelating agents, stabilizers, preservatives, colorants, and fragrances.

Lauric diethanolamide, a nonionic surfactant, is a suitable secondary lathering agent. A cationic surfactant, such as, stearalkonium chloride, or a polyquaternium, i.e., polymeric quaternary ammonium salts such as the quaternary ammonium salt of hydroxyethyl cellulose can be used as a skin substantivity aid. The tetrasodium salt of ethylenediamine tetraacetic acid (EDTA) is a typical chelating agent. Propylene glycol, glycerin or mixtures thereof can be used as stabilizers. Suitable preservatives include methylparaben, propylparaben, formaldehyde and imidazolidinyl urea.

The following examples are illustrative of the invention. All parts and percentages used in this disclosure are by weight unless otherwise indicated.

EXAMPLE 1

The following example illustrates a specific embodiment of the liquid hand soap composition of this invention and how to prepare it.

A liquid hand soap composition using the formulation set forth in Table 1 is prepared by charging a tank with water fitted with a marine propeller stirrer. Stirring is commenced and the preservative is added to the water when a vortex is present. Stirring is continued at room temperature until the preservative is dissolved. The thickener is then added when a vortex is present and stirring is continued until it is dissolved. The resulting aqueous mixture is then transferred to a tank equipped with a paddle stirrer. The stearalkonium chloride and the mixture of sodium alpha-olefin sulfonates having 10 to 14 carbon atoms are added and stirred until dissolved. Stirring is continued and heating is commenced up to 80° C. while the ethylene glycol monostearate is added. Once the ethylene glycol monostearate is dissolved and the resulting mixture is opaque, the heat is turned off. The remaining ingredients are added and stirred until dissolved while the mixture cools to room temperature.

TABLE 1

| Ingredients | % by weight |
| --- | --- |
| A mixture of sodium alpha-olefin sulfonates having 10 to 14 carbon atoms | 3.0 |
| Ethylene glycol monostearate | 1.00 |
| Sodium lauroyl sarcosinate | 2.00 |
| Cocamidopropyl betaine | 2.00 |
| Hydroxyethylcellulose (2.6 hydroxyethyl M.S.; 2100 cps. water viscosity at 25° C. and 1% concentration) | 0.8 |
| Stearalkonium chloride | 0.10 |
| Tetrasodium salt of ethylenediamine tetraacetic acid (EDTA) | 0.3 |
| Propylene glycol | 0.5 |
| Glycerin | 0.5 |
| Methylparaben | 0.1 |
| Distilled water | 89.7 |

The composition is opaque in appearance, has a Brookfield viscosity of 4000 cps. at 25° C. measured by a Brookfield LVT viscometer at 30 rpm, and an active ingredient concentration of 8.8%.

EXAMPLE 2

This example illustrates another specific embodiment of the opaque hand soap composition of this invention.

The procedure of Example 1 and the formulation of Table 1 are used except that a hydroxypropyl guar having 0.5 hydroxypropyl M.S. is used instead of the hydroxyethyl cellulose, except that no glycerin is used, except that a propylene glycol solution of methylparaben, propylparaben and imidazolidinyl urea is used instead of methylparaben, except that 0.2 percent by weight of a 70% sorbitol solution is added, and except that a sufficient amount of citric acid is added to bring the pH to approximately a pH 7.3. The composition has an opaque appearance, a viscosity of 4000 cps. at 25° C. at 30 rpm, and an active ingredient concentration of 8.8%.

EXAMPLE 3

This example illustrates another specific embodiment of the liquid hand soap composition of this invention.

The procedure of Example 1 and the formulation of Table 1 are used except that 0.05 of a polyquaternium-5 is used instead of the stearalkonium chloride, except that a propylene glycol solution of methylparaben, propylparaben and imidazolidinyl urea is used instead of methylparaben and except that no glycerin is used. The composition has an opaque appearance, a viscosity of 2800 cps. at 25° C. at 30 rpm, and an active ingredient composition of 8.8%.

EXAMPLES 4–8

This example illustrates other specific embodiments of the liquid shower soap of the composition of this invention. The procedure of Example 1 and the formulations of Table 2 are used.

TABLE 2

| Ingredients | Examples % by weight | | | | |
| --- | --- | --- | --- | --- | --- |
| | 4 | 5 | 6 | 7 | 8 |
| A mixture of sodium alpha-olefin sulfonates having 10 to 14 carbon atoms (40% active) | 5.0 | 5.0 | 5.0 | 5.0 | 7.5 |
| Ethylene glycol monostearate | 2.0 | 2.0 | 2.0 | 1.0 | 1.0 |

TABLE 2-continued

| Ingredients | Examples % by weight | | | | |
|---|---|---|---|---|---|
| | 4 | 5 | 6 | 7 | 8 |
| Sodium lauroyl sarcosinate (30% active) | 3.33 | 6.66 | 6.66 | 6.66 | 6.66 |
| Cocamidopropyl betaine (30% active) | 3.33 | 3.33 | 6.66 | 6.66 | 6.66 |
| Hydroxypropyl guar (0.5 hydroxypropyl M.S.) | 0.80 | 0.80 | 0.80 | 0.80 | 0.80 |
| Stearalkonium chloride | 0.10 | 0.10 | 0.10 | 0.10 | 0.10 |
| Glycerin | 0.50 | 0.50 | 0.50 | 0.50 | 0.50 |
| Propylene glycol | 0.50 | 0.50 | 0.50 | 0.50 | 0.50 |
| Tetrasodium salt of ethylenediamine tetraacetic acid (EDTA) | 0.30 | 0.30 | 0.30 | 0.30 | 0.30 |
| Methylparaben | 0.10 | 0.10 | 0.10 | 0.10 | 0.10 |
| Water | 84.14 | 80.81 | 77.48 | 78.48 | 75.98 |
| Brookfield viscosity at 25° C. at 30 rpm (cps.) | 3080 | 6400 | 5640 | 3480 | 3420 |
| Active ingredient conc. % | 6.8 | 7.8 | 8.8 | 7.8 | 8.8 |

EXAMPLE 9

This example illustrates another specific embodiment of the liquid hand soap composition of this invention.

The procedure of Example 1 and the formulation of Table 1 are used except that a hydroxypropyl guar having a 0.9 hydroxypropyl M.S. is used in place of the hydroxyethyl cellulose. The composition is opaque in appearance, has a Brookfield viscosity of 3800 cps. at 25° C. at 30 rpm, and has an active ingredient concentration of 8.8%.

The compositions of this invention are readily dispersed by a pump and are freely pourable from a suitable container.

Thus, this invention provides useful opaque liquid hand soap compositions having improved lathering characteristics and increased emollience which contain less than 10% active ingredients.

Features, advantages and other specific embodiments of this invention will become readily apparent to those excercising ordinary skill in the art after reading the foregoing disclosures. In this regard, while specific embodiments of this invention have been described in considerable detail, variations and modifications of these embodiments can be effected without departing from the spirit and scope of the invention as disclosed and claimed.

What I claim and desire to protect by Letters Patent is:

1. A liquid soap composition consisting essentially of, in an aqueous medium, by weight of its principal ingredients,
    (a) from about 40% to about 90% of an anionic surfactant detergent selected from the group consisting of (i) alkylbenzenesulfonates of the formula:

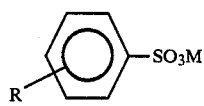

where R is dodecyl and M is sodium, calcium, triethanolammonium, and isopropylammonium; (ii) alpha-olefinsulfonates of the formula:

R'CH=CHSO_3Na where R' is 10-18 carbon atoms and mixtures thereof; and (iii) alkyl sulfates of the formula $R''OSO_3M'$ where R" is lauroyl and M' is sodium, potassium, ammonium, diethanolammonium, and triethanolammonium;
    (b) from about 20% to about 50% of a primary lathering agent selected from the group consisting of (i) dialkyl sulfosuccinates of the formula $RO_2CCH_2CH(SO_3Na)CO_2R$, where R is lauroyl or myristyl, (ii) N-acyl-sarcosinates of the formula $R'CON(CH_3)CH_2CO_2Na$, where R'CO— is lauroyl and cocoyl, (iii) sodium N-acyl-N-methyltaurates of the formula $R''CON(CH_3)CH_2CH_2SO_3Na$, where R"CO is acyl, (iv) sodium cocoylisothionate, (v) amidopropylbetaines of the formula $R'''CONHCH_2CH_2CH_2N^+(CH_3)_2CH_2CO_2^-$, where R'''CO is cocoyl and lauroyl, and (vi) mixtures thereof;
    (c) from about 5% to about 30% of a nonionic surfactant opacifying agent;
    (d) from about 0.5% to about 20% of a primary water-soluble polymer thickener selected from the group consisting of hydroxyethylcellulose and hydroxypropyl guar as its principal ingredients; wherein the total of (a), (b), (c), and (d) is 100% of the principal ingredients; and
    (e) water from about 75% to about 85%.

2. The composition of claim 1 wherein the water-soluble polymer is a hydroxyethyl cellulose having a hydroxyethyl substitution of about 1.6 to about 3.6 M.S. and a water viscosity from about 1500 cps. to about 5000 cps. at 25° C. at 1% concentration at 30 rpm.

3. The composition of claim 1 wherein the water-soluble polymer is a hydroxypropyl guar having a hydroxypropyl substitution from about 0.3 to about 1.2 M.S.

4. The composition of claim 1 wherein the water-soluble polymer is present at a concentration from about 10% to 17%.

5. The composition of claim 1 wherein the water-soluble polymer is present at a concentration from about 10% to about 17%.

6. The composition of claim 1 wherein the water-soluble polymer is present at a concentration from about 10% to about 17%.

7. The composition of claim 1 wherein component (a) is anionic surfactant detergent (i).

8. The composition of claim 1 wherein component (a) is anionic surfactant detergent (ii).

9. The composition of claim 1 wherein component (a) is anionic surfactant detergent (iii).

10. The composition of claim 1 wherein component (b) is anionic surfactant detergent (i).

11. The composition of claim 1 wherein component (b) is anionic surfactant detergent (ii).

12. The composition of claim 1 wherein component (b) is anionic surfactant detergent (iii).

13. The composition of claim 1 wherein component (b) is anionic surfactant detergent (iv).

14. The composition of claim 1 wherein component (b) is anionic surfactant detergent (v).

* * * * *

UNITED STATES PATENT AND TRADEMARK OFFICE
CERTIFICATE OF CORRECTION

PATENT NO. : 4,617,148

DATED : October 14, 1986

INVENTOR(S) : S. J. Shields

It is certified that error appears in the above-identified patent and that said Letters Patent are hereby corrected as shown below:

Column 6, Claim 1 (e) line 32;

"(e) water from about 75% to about 85%"

should read

--(e) water from about 85% to about 94%-- .

Signed and Sealed this

Thirtieth Day of December, 1986

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,617,148
DATED : October 14, 1986
INVENTOR(S) : S. J. Shields

It is certified that error appears in the above-identified patent and that said Letters Patent are hereby corrected as shown below:

Column 1, line 55; delete --1.8-- and substitute "1.6".

Signed and Sealed this

Twenty-fifth Day of August, 1987

*Attest:*

DONALD J. QUIGG

*Attesting Officer*   *Commissioner of Patents and Trademarks*

UNITED STATES PATENT AND TRADEMARK OFFICE
CERTIFICATE OF CORRECTION

PATENT NO.   : 4,617,148

DATED        : October 14, 1986

INVENTOR(S)  : S. J. Shields

It is certified that error appears in the above-identified patent and that said Letters Patent is hereby corrected as shown below:

Column 1, line 55; delete --1.8--and substitute "1.6".

Signed and Sealed this

Fifteenth Day of December, 1987

Attest:

DONALD J. QUIGG

*Attesting Officer*  *Commissioner of Patents and Trademarks*